US011026869B2

(12) United States Patent
Lang et al.

(10) Patent No.: US 11,026,869 B2
(45) Date of Patent: *Jun. 8, 2021

(54) PROCESS FOR PRODUCING SMALL DROPLET EMULSIONS AT LOW PRESSURE

(71) Applicant: Conopco, Inc., Englewood Cliffs, NJ (US)

(72) Inventors: David John Lang, Southbury, CT (US); Congling Quan, Woodbridge, CT (US)

(73) Assignee: CONOPCO, INC., Englewood Cliffs, NJ (US)

( * ) Notice: Subject to any disclaimer, the term of this patent is extended or adjusted under 35 U.S.C. 154(b) by 296 days.

This patent is subject to a terminal disclaimer.

(21) Appl. No.: 16/094,077

(22) PCT Filed: Apr. 4, 2017

(86) PCT No.: PCT/EP2017/057987
§ 371 (c)(1),
(2) Date: Oct. 16, 2018

(87) PCT Pub. No.: WO2017/182265
PCT Pub. Date: Oct. 26, 2017

(65) Prior Publication Data
US 2020/0323748 A1 Oct. 15, 2020

(30) Foreign Application Priority Data
Apr. 21, 2016 (EP) ..................................... 16166488

(51) Int. Cl.
| | | |
|---|---|---|
| *A61K 8/06* | (2006.01) | |
| *A61K 8/31* | (2006.01) | |
| *A61K 8/44* | (2006.01) | |
| *A61K 8/92* | (2006.01) | |
| *A61K 8/36* | (2006.01) | |
| *A61Q 19/10* | (2006.01) | |

(52) U.S. Cl.
CPC .............. *A61K 8/068* (2013.01); *A61K 8/062* (2013.01); *A61K 8/31* (2013.01); *A61K 8/361* (2013.01); *A61K 8/44* (2013.01); *A61K 8/922* (2013.01); *A61Q 19/10* (2013.01); *A61K 2800/10* (2013.01); *A61K 2800/21* (2013.01); *A61K 2800/805* (2013.01)

(58) Field of Classification Search
CPC ... A61K 8/06; A61K 8/31; A61K 8/44; A61K 8/92; A61K 8/36; A61Q 19/10
See application file for complete search history.

(56) References Cited

U.S. PATENT DOCUMENTS

| | | |
|---|---|---|
| 5,500,152 A | 3/1996 | Helliwell |
| 5,584,293 A | 12/1996 | Darrow et al. |
| 6,066,608 A | 5/2000 | Glenn, Jr. |
| 6,488,780 B2 | 12/2002 | Cauwet-Martin |
| 6,541,018 B1 | 4/2003 | Simonnet et al. |
| 8,357,381 B2 | 1/2013 | Eskuchen et al. |
| 8,772,212 B2 | 7/2014 | Restrepo et al. |
| 8,834,903 B2 | 9/2014 | Simonnet et al. |
| 9,132,292 B2 | 9/2015 | Allef et al. |
| 2002/0054861 A1 | 5/2002 | Schmucker et al. |
| 2003/0012759 A1 | 1/2003 | Bowen-Leaver et al. |
| 2003/0077299 A1 | 4/2003 | Iwai et al. |
| 2005/0025957 A1 | 2/2005 | Issberner et al. |
| 2007/0065390 A1 | 3/2007 | Spengler et al. |
| 2008/0241204 A1 | 10/2008 | Leikauf |
| 2014/0113852 A1 | 4/2014 | Martinus et al. |
| 2017/0087064 A1* | 3/2017 | Ikeda ....................... A61K 8/06 |

FOREIGN PATENT DOCUMENTS

| | | |
|---|---|---|
| CA | 2442660 | 10/2002 |
| CN | 101360481 | 2/2009 |
| CN | 103505382 | 1/2014 |
| CN | 105407860 | 3/2016 |
| EP | 0575461 | 12/1993 |
| EP | 105287235 | 2/2016 |
| KR | 20110072022 | 6/2011 |
| KR | 101419602 | 6/2014 |
| KR | 20140066362 | 6/2014 |
| WO | WO9844896 | 10/1998 |
| WO | WO02080864 | 10/2002 |
| WO | WO2015014604 | 2/2015 |

OTHER PUBLICATIONS

Partial Search Report in EP16166486; dated Aug. 1, 2016.
IPRP2 in PCTEP2017057987; Apr. 5, 2018.
Search Report and Written Opinion in PCTEP2017057987; dated Jun. 13, 2017.
Search Report and Written Opinion in EP16166488; dated Aug. 31, 2016.
Search Report and Written Opinion in PCTEP2017057976; dated Jun. 14, 2017.
Search Report and Written Opinion in PCTEP2017057963; dated Jun. 21, 2017.
IPRP2 in PCTEP2017057976; Apr. 5, 2018.
Search Report & Written Opinion in EP16166487; dated Aug. 31, 2016.
Search Report and Written Opinion in EP16166486; dated Nov. 15, 2016.
Cheol Heon Lee et al.; Effect of surfactant mixtures on irritant contact dermatitis potential in man: sodium lauroyl glutamate and sodium lauryl sulphate; Contact Dermatitis; Apr. 1994; pp. 205-209; vol. 30 No. 4.
Co-pending U.S. Appl. No. 16/094,074.
Co-pending U.S. Appl. No. 16/094,069.
IPRP1 in PCTEP2017057963; Oct. 23, 2018.

\* cited by examiner

*Primary Examiner* — Zohreh A Fay
(74) *Attorney, Agent, or Firm* — Krista A. Kostiew

(57) ABSTRACT

The present invention relates to novel process for making oil-in-water nanoemulsions. The oil phase contains oil selected from the group consisting of triglyceride oil and/or petrolatum and a $C_8$ to $C_{16}$ fatty acid just be added during preparation; and the aqueous phase contains specific N-acyl derivatives of carboxylic amino acid as primary emulsifier.

13 Claims, No Drawings

PROCESS FOR PRODUCING SMALL DROPLET EMULSIONS AT LOW PRESSURE

CROSS REFERENCE TO RELATED APPLICATIONS

The present application is a U.S. National Phase Application under 35 U.S.C. § 371 of International Application No. PCT/EP2017/057987, filed on Apr. 4, 2017, which claims priority to European Patent Application No. 16166488.3, filed on Apr. 21, 2016, the contents of which are incorporated herein in their entireties.

FIELD OF THE INVENTION

The present invention relates to a process to produce oil-in-water (o/w) nanoemulsions at low pressure (500 psi or less). The process requires the addition of $C_8$ to $C_{18}$ fatty acid to nanoemulsions containing (1) an internal oil phase having triglyceride oils and/or petrolatum; and (2) an external aqueous phase containing surfactants which are salts of N-acyl derivatives of dicarboxylic amino acids (e.g., aspartic acid, glutamic acid), salts of N-acyl derivatives of monocarboxylic acids (e.g., alanine, glycine); or mixtures of such derivatives of mono- and di-carboxylic amino acids.

The invention is concerned with the provision of such triglyceride oils and petrolatum (benefit agents delivered from nanoemulsion) in small droplets (e.g., 600 nanometers or less), which are more aesthetically pleasing than compositions in which benefit agents are delivered in the form of larger oil droplets. Preparing such nanoemulsions at low pressure results in tremendous energy savings, increased production flexibility, significantly lower capital investment for equipment, lower equipment maintenance requirements, less downtime during operation, and improved operating safety.

Nanoemulsions using N-acyl derivatives of amino acid surfactants as emulsifier are claimed in two co-pending applications.

BACKGROUND OF THE INVENTION

Skin moisturizing oils (including triglyceride oils and petrolatum benefit agents noted above) are often delivered from personal cleansing compositions (e.g., shower gels, facial and hand cleansers designed to cleanse and moisturize skin) in the form of large oil drops (e.g., 50 to 200 microns or greater).

U.S. Pat. Nos. 5,584,293 and 6,066,608, both to Glenn, Jr., for example, disclose a moisturizing liquid personal cleansing emulsion with at least 10% lipophilic skin moisturizing agent droplets having a diameter of greater than 200 microns.

U.S. Pat. No. 8,772,212 to Restrepo et al. discloses an isotropic cleansing composition containing high level of petrolatum; greater than 50% by volume of the petrolatum particles have a diameter greater than 50, 100, 150 or 200 microns.

Compositions containing large oil drops need to be well structured so they can suspend the large droplets (using, for example, stabilizers). U.S. Pat. Nos. 5,854,293 and 6,066,608, for example, utilize stabilizers selected from crystalline, hydroxyl-containing stabilizers, polymeric thickeners, C10-C18 diesters, amorphous silica or smectite clay. Special blending processes are typically needed to prepare such compositions. For example, compositions must be prepared under low shear to prevent oil droplet size reduction (see U.S. Pat. No. 8,772,212). Although they provide enhanced delivery of benefit agents, these products are generally considered to be less aesthetically appealing to the consumer due to the presence of large oil droplets that may create a lumpy appearance.

Another method of enhancing the delivery of a benefit agent (e.g., silicone) to the skin, for example, is through the use of cationic hydrophilic polymers such as, for example, hydroxypropyltrimethylammonium derivative of guar gum, sold under the name JAGUAR® C-13-S (see U.S. Pat. No. 5,500,152 to Helliwell). In this reference, silicone oil is a preformed emulsion with oil droplet size ranging from 0.1-1 micron (μm), with a mean particle size of 0.4 μm (there is no mention whether this refers to number average or volume average diameter of droplets). This kind of product tends to be smooth and aesthetically appealing. However, nourishing vegetable oils (triglyceride oils) and highly occlusive skin protectants, such as petrolatum, are typically preferred moisturizers from a cleansing composition.

One challenge facing cleansing compositions that are rich in moisturizing oils is that large amount of oils tend to depress the lather speed and volume.

It is therefore desirable to prepare a personal cleansing composition consisting of triglyceride oils and/or petrolatum nanoemulsion, which is aesthetically appealing, high in deposition of these moisturizing oils, and which maintains high lather performance.

In the subject invention, applicants provide a novel process for making nanoemulsions (themselves novel) for delivery of triglyceride oils and petrolatum as small (100 to 600 nanometers, particularly 50 to 575, more particularly 20 to 400) volume average diameter droplets. This process uses low pressure which results in energy savings, production flexibility, significantly lower initial capital investment for equipment, lower equipment maintenance requirements, less downtime during operation, and improved operating safety.

In two co-pending applications, applicants claim nanoemulsions. In one, use of fatty acid in internal oil phase is not required. In the other, such fatty acids are required. Addition of fatty acid is also required for the low pressure process of the subject matter.

Nanoemulsions made by the process of the invention comprise (1) an oil phase containing benefit agent droplets selected from the group consisting of triglyceride oils, petrolatum and mixtures thereof; and $C_8$ to $C_{18}$ fatty acid co-emulsifier and (2) an aqueous phase comprising one or more surfactants (primary emulsifier) which are salts of N-acyl derivatives of dicarboxylic amino acid, salts of N-acyl derivatives of monocarboxylic acids or mixtures of such salts; specifically, these surfactants may be selected from (a) acylglutamate salt, acylaspartate salt, acylglycinate salt, acylalaninate salt, with defined N-acyl groups, or (b) mixtures of any of these salts.

The specific N-acyl derivatives of amino acids (aspartic acid, glutamic acid, glycine and alanine) typically comprise 50% or greater, preferably 60% or greater, more preferably 70% or greater of all surfactants present in the aqueous phase of the nanoemulson composition.

Both U.S. Pat. Nos. 8,834,903 and 6,541,018 to Simonnet et al. disclose nanoemulsion compositions in which acylglutamate is mentioned as possible surfactant (e.g., U.S. Pat. No. 8,834,903 at column 4, lines 27-31). A process to make the specific emulsions of our invention is not disclosed. There is no recognition of the need for $C_8$ to $C_{18}$ fatty acid to ensure formation of small droplets even when utilizing a low pressure process.

US2003/0012759 A1 to Bowen-Leaver teaches preparation of nanoemulsion using high pressure devices at about 10,000 to 20,000 psi and with multiple passes ([0021] on page 3). It discloses an emulsifier system consisting of anionic surfactant (sodium stearoyl glutamate), non-ionic surfactants (glyceryl stearate/PEG-100 stearate) and stearic acid in Example 1. Fatty acid is used with glyceryl stearate/PEG-100 stearate as co-emulsifiers in oil phase. There is no mention of criticality of combining acyl glutamate (anionic surfactant) and fatty acid as emulsifiers to improve production efficiency of nanoemulsion. In our application, non-ionic emulsifiers, such as glyceryl stearate and PEG-100 stearate, are not included in the emulsifier system for preparing nanoemulsions. The combination of acyl glutamate and fatty acid has been found to unexpectedly reduce petrolatum nanoemulsion droplet size to below 300 nm after only one pass and at 450 psi or less, without any other non-ionic surfactants present. Such process efficiency, based on use of fatty acid, is completely unpredictable.

BRIEF DESCRIPTION OF THE INVENTION

Specifically, the present invention relates to a process for forming nanoemulsion compositions comprising:
a) an internal oil phase comprising (i) 40 to 75% by wt. of total nanoemulsion of oil selected from the group consisting of triglyceride oil, petrolatum and mixtures thereof, wherein the melting point of the petrolatum is 30 to 60° C.; and (ii) 1.1 to 8%, preferably 1.2 to 6% by wt. nanoemulsion of a $C_8$ to $C_{18}$, preferably $C_{10}$ to $C_{14}$ fatty acid (e.g., $C_{12}$ lauric acid), and
b) an external aqueous phase comprising 1 to 15% by wt. (as active) of total nanoemulsion of a surfactant or surfactants which are N-acyl derivatives of amino acid and, preferably, said surfactant or surfactants is selected from the group consisting of
(i) salt of N-acyl derivative of di-carboxylic amino acid (e.g., acylglutamic acid or acylaspartic acid), wherein greater than 65% (e.g., 65 to 100%, preferably 65 to 90%) of the acyl group has chain length of $C_{14}$ or less;
(ii) salt of N-acyl derivatives of mono-carboxylic amino acid (e.g., acylglycinate, acylalanate), wherein greater than 65% of the acyl group (e.g., 65 to 100%, preferably 65 to 90%) has chain length $C_{14}$ or less; and
(iii) mixtures thereof;
wherein the surfactant of (b) comprises 50% or greater, preferably 60% or greater, preferably 70% or greater, preferably 75 to 100% of all surfactants present in the aqueous phase of the nanoemulsion;
wherein the volume average diameter of the oil droplets of (a) is 20 to 600 nanometers,
wherein said process comprises:
1) adding the $C_8$ to $C_{18}$ fatty acid of component (a)(ii) to oil of (a)(i);
2) heating oil phase (a) to a sufficient temperature to ensure that it is completely molten and is one clear homogeneous liquid. Practically, this means heating the oil phase to a temperature above the melting point of all components of the mixture including fatty acids and petrolatum. The melting point of all components can be determined by standard differential calorimetry. With the oil phase components of our invention, this typically means heating the oil phase to a temperature range of 45 to 75° C.; and 3) Heating the aqueous phase to a temperature range of 45 to 75° C.
4) Simultaneously pumping the heated aqueous and oil phases via a sonolator or a homogenizer using process pressure of 500 pounds per square inch (psi) or less.

Preferably, a minimum of 1.2% to 1.3% or 1.5% by wt. nanoemulsion fatty acid in the molten oil phase is required to ensure such low pressure processing can be used to obtain particles of desired size.

By adding a fatty acid as co-emulsifier to the oil phase, nanoemulsions of the invention will typically have volume average diameter of droplets of 600 or less; or 575 or less; or 500 or less, or 100 to 600; or 50 to 575. Lower limit can be 20 or 50 or 100 or 125 or 150 or 175. Upper limit can be 300 or 400 or 500 or 575 or 600.

The nanoemulsions of the invention are typically prepared, as noted, by mixing the oil phase (to which fatty acid has been added) and the aqueous phase using a homogenizer or a sonolator operating at pressures at or below 500 psi. Using the same components, but no $C_8$ to $C_{18}$ fatty acid as co-emulsifier in the oil phase, this process would only form a coarse emulsion that would then require homogenization in a second step carried out at much higher pressure (up to 5000 psi) to achieve a finished nanoemulsion with the same droplet size.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

The present invention provides a novel process for making nanoemulsions containing a specific selection of oils and surfactants. The nanoemulsions can be prepared using processing pressure of 500 psi or less. The novel nanoemulsions are ideally suited for use in liquid cleansing compositions, for example, structured (e.g., micellar or lamellar structured) liquid cleansing compositions.

The nanoemulsions of the invention are defined with more particularity below.

Oil Phase

Oils in the oil phase of the nanoemulsions may be triglyceride oil or oils (animal and/or vegetable oils); petrolatum; or mixtures of one or more triglyceride oil.

Examples of triglyceride oils which may be used include soybean oil, sunflower seed oil, coconut oil, rapeseed oil, palm oil, palm kernel oil, grape seed oil and fish oil. Soybean and sunflower seed oils are preferred triglycerides.

The oil in the oil phase may also be petrolatum. The petrolatum preferably has a melting point ranging from 30° to about 60° C. Examples of such petrolatum oils include Vaseline® Petrolatum Jelly from Unilever, WHITE PETROLATUM USP from Calumet Penreco, Petrolatum G2212 and White Protopet® 1S from Sonneborn.

The oils can range from 40% to 75% by wt. of the total nanoemulsion composition. The preferred volume average diameter of the triglyceride oil or petrolatum droplets is 100 to 600 nm, preferably 50 to 575 nm, more preferably 20 to 400 nm. Lower limit can be 20 or 50 or 100 or 125 or 150 nm; and upper limit can be 250 or 300 or 400 or 500 or 575 or 600 nm.

The choice of triglyceride oils and petrolatum helps impart emolliency and occlusivity to skin when the triglyceride oils and/or petrolatum deposit onto skin after the skin is washed with fully formulated cleansing compositions into which the nanoemulsions of this invention have been incorporated.

In addition to the triglyceride oil (or oils) and/or petrolatum, the oil phase may comprise oil soluble skin beneficial actives such as, for example, Vitamin A, Vitamin E, sun screen, fragrances, retinol palmitate, 12-hydroxy stearic acid, conjugated linoleic acid; antibacterial agents; mosquito repellents etc. at level of 0.01 to 5%.

Another ingredient which might be found in the oil phase is an oil phase stabilizer. For example, small amounts (0.01 to 2%, preferably 0.1-1% by wt. nanoemulsion) of antioxidant may be used. When the oil used is triglyceride, a preferred antioxidant which may be used is butylated hydroxytoluene (BHT). This is often used as a food grade antioxidant.

Greater than 1.0% to 8%, preferably 1.1 to 8%, more preferably 1.2 to 6% by wt. total nanoemulsion is comprised of $C_8$ to $C_{18}$, preferably $C_{10}$ to $C_{14}$ fatty acid. Examples of fatty acid are lauric acid, myristic acid, coconut fatty acid and their mixtures. This co-emulsifier is required to ensure low pressure can be used and still produce drops of 600 nm or less. For example, oil phase may contain petrolatum ranging from 40 to 70% by wt. of nanoemulsion and lauric acid 1.1 to 8% by wt. of nanoemulsion.

The fatty acid preferably is present at level of 1.2% by wt. of nanoemulsion, or 1.3% or 1.5% or 2.0% or 2.5 or 3.0% or 3.5% or 4.0%; preferred range is 1.5 to 5.0% or 2.0 to 4.0% or 2.5 to 4.0%.

Aqueous Phase

The aqueous phase contain salts of N-acyl derivatives of amino acids as primary emulsifier (50% or greater, preferably 60% or greater of all surfactant present in the aqueous phase of the nanoemulsion). Preferred emulsifiers are acylglutamate, acylaspartate, acylglycinate and acylalaninate surfactants. Preferably, these are potassium and/or sodium salts of acylglutamate or acyl aspartate or acylglycinate or acylalaninate, wherein greater than 65% of the acyl chains has chain length $C_{14}$ or less, e.g., $C_8$ to $C_{14}$ (e.g., derived from coconut fatty acid). The acyl chains preferably have greater than 75%, more preferably greater than 80% $C_{14}$ or less chain length. Preferably, greater than 75%, most preferably greater than 80% of the chain length are $C_{12}$, $C_{14}$ or mixtures thereof. These predominantly short chain acyl groups (relative to longer chain $C_{16}$ and $C_{18}$, for example) ensure that, when nanoemulsions of the invention are incorporated into fully formulated liquid cleansing compositions (especially structured liquid cleansing compositions), they help maintain or enhance foaming capacity.

There are two formats of amino acid surfactants commercially available. One is powder or flake format, which is typically more expensive and high in purity. Examples of solid dicarboxylic amino acid surfactants include:

sodium N-cocoyl-L-glutamate (e.g., Amisoft® CS-11 by Ajinomoto)
sodium N-lauroyl-L-glutamate (e.g., Amisoft® LS-11 by Ajinomoto)
sodium N-myristoyl-L-glutamate (Amisoft® MS-11 by Ajinomoto)
potassium N-cocoacyl_l-Glutamate (e.g., Amisoft® CK-11 by Ajinomoto)
potassium N-myristoyl-L-glutamate (Amisoft® MK-11 by Ajinomoto)
potassium N-lauroyl-L-glutamate (Amisoft® LK-11 by Ajinomoto)
Sodium Lauroyl Aspartate (AminoFoamer™ FLMS-P1 by Asahi Kasei Chemical Corporation)
Sodium Lauroyl Glutamate (Aminosurfact™ ALMS-P1/S1 by Asahi Kasei Chemical Corporation)
Sodium Myristoyl Glutamate (Aminosurfact™ AMMS-P1/S1 by Asahi Kasei Chemical Corporation)

Examples of solid monocarboxylic amino acid surfactants include:
sodium cocoyl glycinate (e.g., Amilite® GCS-11 by Ajinomoto)
potassium cocoyl glycinate (e.g., Amisoft® GCK-11 by Ajinomoto)

In addition to the amino acid surfactants noted above (which are in powder form and are not convenient to handle in plant production), using fatty acid as co-emulsifier permits use of amino acid surfactants in liquid form, which is typically less expensive but high in pH and inorganic salt. The use of a fatty acid as co-emulsifier, especially lauric acid, in conjunction with the industrial liquid amino acid surfactant resulted in the formation of stable emulsions and the efficient formation of smaller oil droplets to form a highly superior nanoemulsion. Oil droplet sizes below 600 nm were produced using process pressure of 500 psi or less.

Liquid amino acid surfactants typically contains 20~35% surfactant active, high in pH and inorganic salt (e.g. 3 to 6% NaCl). Examples include:
AMISOFT® ECS-22SB: Disodium Cocoyl Glutamate (30% Aqueous Solution)
AMISOFT® CS-22: Disodium Cocoyl Glutamate sodium Cocoyl Glutamate (25% Aqueous Solution)
AMISOFT® CK-22: Potassium Cocoyl Glutamate (30% Aqueous Solution)
AMISOFT® LT-12: TEA-Lauroyl Glutamate (30% Aqueous Solution)
AMISOFT® CT-12 TEA-Cocoyl Glutamate (30% Aqueous Solution)
AMILITE® ACT-12: TEA-Cocoyl Alaninate (30% Aqueous Solution)
AMILITE® ACS-12: Sodium Cocoyl Alaninate (30% Aqueous Solution)
AMILITE® GCK-12/GCK-12K: Potassium Cocoyl Glycinate (30% Aqueous Solution)
Aminosurfact™ ACDS-L: Sodium Cocoyl Glutamate (25% Aqueous Solution)
Aminosurfact™ ACDP-L: Potassium Cocoyl Glutamate (22%)+Sodium Cocoyl Glutamate(7%)
Aminosurfact™ ACMT-L: TEA-Cocoyl Glutamate (30% Aqueous Solution)

AminoFoamer™ FLDS-L: Sodium Lauroyl Aspartate (25% Aqueous Solution)

In addition to Amisoft and Amilite series from Ajinomoto, Aminosurfact™ and AminoFoamer™ from Asahi Kasei Chemical Corporation), other suppliers of liquid amino acid surfactants include Clariant (e.g. Hostapon SG Sodium cocoyl glycinate), Solvay (e.g. Geropon® PCG Potassium Cocoyl Glutamate aqueous solution; Gerapon® LG 3S sodium lauryl glycinate with glycerin), Galaxy (Galsoft® KCGL Potassium Cocoyl Glutamate aqueous solution; GalSoft® SCG plus sodium cocoyl glycinate, 20% active) and Sino Lion (Eversoft® USK-30K Potassium Cocoyl Glutamate aqueous solution; Eversoft® YCS-305 sodium cocoyl glycinate).

Additionally, other mild cleansing surfactants can be used in the aqueous phase. Anionic surfactants which may be used include sodium cocoyl isethionate, sodium lauroyl isethionate, and other amino acid based surfactants, such as sodium lauroyl sarcosinate, sodium cocoyl sarcosinate. Amphoterics such as coco betaine, cocamidopropyl betaine, sodium lauroamphoacetate, Lauramidopropyl hydroxysultaine and Cocamidopropyl hydroxysultaine can also be used. These co-surfactants are typically present at a level of 50% or less, preferably 40% or less, preferably 30% or less of total surfactants in the aqueous phase of the nanoemulsion.

Overall surfactants in aqueous phase comprise 1 to 15% preferably 4 to 12% by wt. of total nanoemulsion. As indicated, the salts of N-acyl derivatives of amino acid, preferably acylglutamate, acylaspartate, acyl acylglycinate, acylalaninate or mixtures thereof are the principal surfactant of the nanoemulsion. They constitute 50% or greater, preferably 60% or greater of all surfactant in the aqueous phase. Preferably they constitute greater than 70% or greater, more preferably 75% or greater. They may of course be the only surfactant present.

Preferably, the aqueous phase may contain a preservative or preservatives. Typically, they are present at a level of 0.01 to 1.0%, preferably 0.1 to 0.5% by wt.

Nanoemulsions of the invention, have volume average diameter (also used interchangeably in and with terms "volume mean diameter" or "volume average size") of 600 nm or less, preferably 50 nm to 575 nm, more preferably 100 to 400 nm. Lower and upper limit may be as previously defined.

Nanoemulsions with droplet sizes of these ranges are obtained in the subject invention using low pressure (500 psi or less) flow in a homogenizer or sonolator. Specifically, pressure per square inch (psi) can be an upper range of 500 or 450 or 400 psi and lower range of 250 or 300 or 350 psi. A preferred range is 300 to 400 psi.

Preparation of Nanoemulsion

Nanoemulsions are formed as noted below.

First, it is critical to ensure that fatty acid (e.g., 1.1 to 5% by wt. of nanoemulsion) is added to oil. The oil phase and aqueous phase were heated up to 75° C. separately such that it was clear and uniform; then simultaneously pumping the aqueous and oil phases via a sonolator or a homogenizer at pressures no higher than 500 psi. Pressures higher than 500 psi are not required for nanoemulsion formation in this invention. The emulsion may be created by using a homogenizer operating at low pressure (500 psi or less). One example is the standard Sonolator device produced by Sonic Corporation of Connecticut, for example, these standard sonolators are normally operated at pressures of 200-500 psi to form the emulsion.

In the examples, the following terms are defined as noted below:

D[4, 3]: volume average diameter or volume mean diameter or volume average size The average diameters are determined by a Malvern Mastersizer.

Comparative A and Examples 1-6: 50-55% Petrolatum was used to form nanoemulsions, with either potassium cocoyl Glutamate or Sodium cocoyl glycinate in the liquid form as primary emulsifier, ranging 4 to 8.2% in active and lauric acid as co-emulsifier ranging 1 to 4%. The emulsion was prepared by a low pressure sonolator at a pressure up to 450 psi, where the molten oil phase and aqueous phase at 60~75 C were simultaneously pumped through the orifice of low pressure sonolator and thus formed the emulsion.

As seen from Examples 1-6

| Ingredient | Comparative A Wt. % | Example 1 Wt. % | Example 2 Wt. % | Example 3 Wt. % | Example 4 Wt. % | Example 5 Wt. % | Example 6 Wt. % |
|---|---|---|---|---|---|---|---|
| Oil Phase | | | | | | | |
| Petrolatum G2212 | 55% | 55% | 55% | 55% | 55% | 55% | |
| Whiter petrolatum | | | | | | | 50% |
| Lauric acid | 1% | 2% | 2% | 4% | 4% | 4% | 4% |
| Aqueous Phase | | | | | | | |
| Potassium Cpocoyl Glutamate (Galaxy, Galsoft KCGL, Active 30%) | 27.3% (8.2% active) | 27.3% (8.2% active) | 13.3% (4% active) | 13.3% (4% active) | 20% (6% active) | 27.3% (8.2% active) | |
| Sodium cocoyl glycinate (Galsoft SCG Plus Active 20%) | | | | | | | 40% (8%) |
| Deionized water | Q.S. | Q.S. | Q.S. | Q.S. | Q.S. | Q.S. | Q.S. |
| DMDM Hydantoin (and) | 0.158% | 0.158% | 0.158% | 0.158% | 0.158% | 0.158% | 0.4% |

-continued

| Ingredient | Comparative A Wt. % | Example 1 Wt. % | Example 2 Wt. % | Example 3 Wt. % | Example 4 Wt. % | Example 5 Wt. % | Example 6 Wt. % |
|---|---|---|---|---|---|---|---|
| Iodopropynyl Butylcarbamate (Glydant™ Plus™ Liquid) | | | | | | | |
| $D_{[4,3]}$, nm (@450 psi) | 855 | 514 | 560 | 350 | 279 | 285 (350 psi) | 334 (350 psi) |

As seen from Examples 1-6, use of greater than 1.0% $C_8$ to $C_{18}$ fatty acid (e.g., lauric) allow low pressure process to be used while yielding droplet size under 600 nm.

Efficient production of small droplets is not believed to be just function of total surfactant amount, but rather of type and interaction of surfactants. This is seen comparing Example 1 to Example 4. Although there is almost equal overall surfactant active in Example 1 (10.2% vs. 10% in Example 4), because of interaction of anionic glutamate and greater amounts of fatty acid, the droplet size for petrolatum of Example 4 is 279 nm versus 514 nm for Example 1.

The invention claimed is:

1. A process for making a nanoemulsion composition comprising:
   a) an internal phase comprising (i) 55 to 75% by wt. of total nanoemulsion composition of oils selected from the group consisting of triglyceride, petrolatum and mixtures thereof, wherein the melting point of the petrolatum is 30 to 60° C.; and (ii) 1.1 to 8% by wt. nanoemulsion of a $C_8$ to $C_{18}$ fatty acid; and
   b) an external aqueous phase comprising 2 to 15% by wt. of total nanoemulsion composition of a surfactant or surfactants which are N-acyl derivatives of amino acid salt;

wherein the surfactant of (b) comprises 50% or greater of all surfactant present in said external aqueous phase;
wherein the volume average diameter of droplets of (a) is 20 to 600 nanometers,
wherein said process comprises:
   1) adding the $C_8$ to $C_{18}$ fatty acid of component (a)(ii) to oil of (a)(i);
   2) heating oil phase (a) to a sufficient temperature so that all compounds are molten; and
   3) Heating the aqueous phase to a temperature range of 45 to 75° C.; and
   4) Simultaneously pumping the heated aqueous and oil phases via a sonolator or a conventional homogenizer using process pressure of 500 pounds per square inch (psi) or less.

2. The process according to claim 1, wherein said surfactant or surfactants are selected from the group consisting of (i) salt of N-acyl derivatives of dicarboxylic amino acid, wherein greater than 65% to 100% of the acyl group has chain length of $C_{14}$ or less; and
(ii) salt of N-acyl derivatives of monocarboxylic amino acid, wherein 65% to 100% of the acyl group has chain length $C_{14}$ or less; and
(iii) mixtures thereof.

3. The process according to claim 2, wherein the N-acyl derivative of dicarboxylic amino acid is a salt of acylglutamic acid, salt of acylaspartic acid or mixture thereof.

4. The process according to claim 2, wherein the salt of N-acyl derivative of monocarboxylic amino acid is a salt of acylglycinate, salt of acylalaninate or mixture thereof.

5. The process according to claim 1, wherein volume average diameter of the droplets is 100 to 500 nm.

6. The process according to claim 1, wherein volume average diameter of droplets is 70 to 400 nm.

7. The process according to claim 1, wherein the oil is a triglyceride oil and said triglyceride oil is selected from the group consisting of soybean oil, sunflower seed oil, coconut oil, rapeseed oil, palm oil, palm kernel oil, grape seed oil, fish oil and mixtures thereof.

8. The process according to claim 1, wherein the oil is petrolatum and the melting point of the petrolatum is 30 to 60° C.

9. The process according to claim 1, wherein the oil mixture is a mixture of triglyceride oil and petrolatum.

10. The process according to claim 1, wherein the fatty acid having a chain length $C_8$-$C_{18}$, is selected from the group consisting of lauric acid, myristic acid, coconut fatty acid and their mixtures, most preferably, lauric acid.

11. The process according to claim 1, wherein the fatty acid is at least 1.5 to 8% by wt. of total nanoemulsion.

12. The process according to claim 1, wherein the salts of acylglutamate acylaspartate, acylglycinate, and acylalaninate are sodium and/or potassium salts.

13. The process according to claim 1, wherein the nanoemulsion is prepared at pressure from a homogenizer or sonolator and said pressure is 150 to 450 psi.

* * * * *